(12) United States Patent
Groen

(10) Patent No.: US 6,200,283 B1
(45) Date of Patent: Mar. 13, 2001

(54) REFLEX ZONE MASSAGE STIMULATOR

(75) Inventor: Johannes Groen, Marbella (ES)

(73) Assignee: Casa Verde Investments Ltd. (GB)

( * ) Notice: Subject to any disclaimer, the term of this patent is extended or adjusted under 35 U.S.C. 154(b) by 0 days.

(21) Appl. No.: 09/297,007

(22) PCT Filed: Sep. 23, 1997

(86) PCT No.: PCT/EP97/05277

§ 371 Date: Jun. 18, 1999

§ 102(e) Date: Jun. 18, 1999

(87) PCT Pub. No.: WO98/17223

PCT Pub. Date: Apr. 30, 1998

(30) Foreign Application Priority Data

Oct. 24, 1996 (NL) .................................................. 1004358

(51) Int. Cl.$^7$ .................................................. A61H 19/00
(52) U.S. Cl. .......................... 601/136; 601/101; 601/117
(58) Field of Search .............................. 601/84–90, 136, 601/93, 103, 117

(56) References Cited

U.S. PATENT DOCUMENTS

| | | |
|---|---|---|
| 1,722,866 | 7/1929 | Snider . |
| 2,080,208 | 5/1937 | Illch . |
| 3,037,500 | 6/1962 | Daugherty . |
| 5,123,406 | * 6/1992 | Masuda . |

FOREIGN PATENT DOCUMENTS

| | | |
|---|---|---|
| 1132418 | 9/1982 | (CA) . |
| 472799 | 4/1929 | (DE) . |
| 2831132 | 1/1979 | (DE) . |
| 0 465 348 | 8/1992 | (EP) . |
| 331098 | 11/1930 | (GB) . |

* cited by examiner

Primary Examiner—Michael A. Brown
Assistant Examiner—Lalitta M. Hamilton
(74) Attorney, Agent, or Firm—Jeffrey D. Myers

(57) ABSTRACT

The invention relates to a reflex zone massage stimulator, particularly for the hand or the foot, comprising a rotatable rod-like element provided with projections, the ends of which define an active surface to be brought into contact with the skin of the user, the active surface being curved such that, viewed in the longitudinal direction of the rod-like element, the distance from said surface to the rotation axis of the element varies. A plurality of projections is farmed as electrode projection for electro-neuro stimulator pulses and is preferably connected with an electrode strip or is formed as one part with said electrode strip. For an effective stimulation of the reflex zones of the foot, the active surface of the relex zone massage stimulator may comprise at least one substantially convex portion and/or at least one substantially concave portion. The reflex zone massage stimulator may further be provided with at least one projectionless portion having a diameter which is larger than the largest diameter of the active surface.

26 Claims, 1 Drawing Sheet

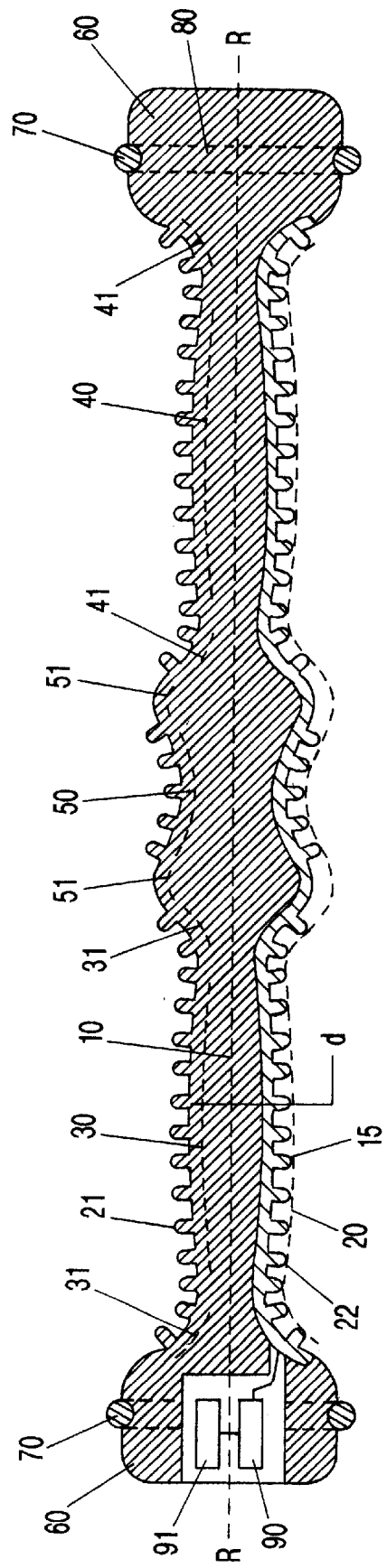

REFLEX ZONE MASSAGE STIMULATOR

The present invention relates to a reflex zone massage stimulator, particularly for the hand or the foot, comprising a rotatable rod-like element provided with projections, the ends of which define an active surface to be brought into contact with the skin of the user.

Such a massage stimulator is known from WO-A-94/1353. The massage stimulator described therein comprises a cylindrical element having a circular cross section and the surface of the cylindrical element being provided with projections. The element is rotatably mounted in a handle part, by which the cylindrical element with the projections can be rolled over a body part for massaging.

There are a few disadvantages and problems associated with this massage stimulator. One disadvantage of this massage stimulator is that it is mainly suitable for massaging substantially flat surfaces. The massage is less efficient on curved body parts such as is the case with, for instance, the foot with its various parts.

It is the objective of the invention to provide a massage stimulator of the kind mentioned in the preamble, in which said disadvantages are precluded.

To this end the reflex zone massage stimulator according to the invention is characterized in that the active surface, which is defined by the ends of the reflex zone massage stimulator's projections, is curved such that, viewed in the longitudinal direction of the rod-like element, the distance from this surface to the rotation axis of the element varies. The reflex zone massage stimulator can be designed such as to allow, for instance, the feet to be massaged in an effective manner. The feet may now not only be massaged flat but also laterally. Practice has shown this to result in improved massaging of the feet.

In a preferred embodiment a plurality of projections is formed as electrode projections for electro-neuro stimulator pulses. This allows the reflex zones in, for instance, the foot or the hand to be stimulated more effectively. By means of said electro-neuro stimulator pulses (Transcutane Electro-NeuroStimulator pulses, TENS-pulses) which are conveyed to the reflex zones via the skin, the effect of the reflex zone massage stimulator is considerably improved and accelerated.

In a convenient embodiment the electrode projections are connected with an electrode strip. The electrode projections are now electrically coupled by means of the electrode strip. By connecting the strip at one point with a pulse-generating device, all electrode projections connected with the strip can be provided with electro-neuro stimulator pulses, without having to connect each individual electrode projection with the pulse-generating device separately. By means of the electrode strip, the massage stimulator with electrode projections is easy to manufacture.

An advantageous embodiment is characterized in that the electrode projections and the electrode strip are formed as one part. As a result, the manufacture of the massage stimulator is considerably streamlined.

Preferably a plurality of rows of electrode projections are provided in the at least approximately longitudinal direction of and around the rod-like element alternating with rows of non-electrode projections provided in the at least approximately longitudinal direction of the rod-like element. When using the reflex zone massage stimulator, the reflex zones are now alternatingly stimulated by electrode projections and electro-neuro stimulator pulses and by non-electrode projections, which further improves the effect of the massage stimulator.

There are different ways for obtaining the curved active surface. In two possible variants the rod-like element may in the longitudinal direction have a varying diameter while the length of the projections remains constant, however, the diameter of the rod-like element may in the longitudinal direction also remain constant while the length of the projections varies.

The active surface of the massage stimulator may be designed in several ways. It may comprise at least one substantially convex portion and/or at least one substantially concave portion. Both forms allow the user to, for instance, massage the feet in a different manner or to massage different parts of the feet.

In a particular embodiment the reflex zone massage stimulator is characterized by at least two substantially convex or concave portions which, in relation to each other, possess a different degree of convexity and concavity respectively. Portions having in relation to each other a different degree of convexity or concavity, afford the possibility to stimulate the feet in a somewhat different manner during massage.

In a favourable embodiment of the invention, the massage stimulator is characterized in that the reflex zone massage stimulator comprises at least one projection-less portion having a diameter which is larger than the largest diameter of the active surface. By placing the reflex zone massage stimulator on the floor or another surface and by placing on it, for instance, both feet or both hands and moving them to and fro, the reflex zone massage stimulator will, in the case of the feet, roll under the feet allowing the sole of the foot, the left and the right side of the foot, the heel and the toes to be massaged effectively. This manner of use of the reflex zone massage stimulator affords an important advantage compared with the known reflex zone massage stimulator. The feet can now be massaged by the user, without requiring the assistance of another person.

In a particular embodiment the reflex zone massage stimulator is characterized by two projection-less portions having a larger diameter and being positioned at the ends of the element. This positioning of the projection-less portions affords the reflex zone massage stimulator greater stability so that it is also possible, for instance, to move said reflex zone massage stimulator over the floor with one foot.

In a preferred embodiment the massage stimulator is characterized in that the projection-less portions having a larger diameter are provided with a surrounding elastic element. This provision affords the reflex zone massage stimulator a better grip on the surface so that it slips less easily during use. In this manner the production of noise when rolling on hard surfaces is also reduced.

In a particularly advantageous embodiment the elastic elements are rings which are partially admitted into grooves provided in the surface of the projection-less portions having a larger diameter. Placement and possible replacement of these rings around the projection-less portions is simple. Due to the grooves the rings will remain in place and will not slide off the projection-less portions during rolling.

Preferably the active surface is designed such that there is a gradual transition between the different portions of the active surface of the reflex zone massage stimulator. An abrupt transition between the different portions could result in irritations during massage. In addition, it is now possible to adapt the reflex zone massage stimulator even better to the anatomy of, for instance, the foot.

In a favourable embodiment the projections are placed substantially perpendicular on the surface of the rod-like element. In this manner the massage will provide the most effective stimulation of the reflex zones of, for instance, the feet.

An effective embodiment of the reflex zone massage stimulator is characterized in that the projections are made from an elastic material. Preferably the projections are made from an plastic having a Shore hardness of about 50 to 90, and more preferably from a plastic having a Shore hardness of about 75. During massage the projections will then yield a little to pressure, preventing excessive stimulation and irritation of the skin. Using said elastic material also makes the reflex zone massage stimulator more comfortable.

A favourable embodiment is characterized in that the rod-like element and the non-electrode projections are manufactured as one part from one material. This means that the manufacture of the reflex zone massage stimulator can be simpler and consequently cheaper and the loss of projections is avoided.

The invention will now be further elucidated with reference to the drawing in which the only FIGURE shows a schematic longitudinal section of a preferred embodiment of the invention.

A rotatable rod-like element 10 is provided with projections 21, 22. These projections 21, 22 may be designed in various ways and in the embodiment shown they are rodlets. The ends of said projections 21, 22 define an active surface 20 intended to contact the skin of the user.

To obtain effective massage stimulation of the reflex zones of, for instance, the feet or the hands, said active surface 20 is curved. In the embodiment shown, the active surface comprises two substantially convex portions 30, 40 and one substantially concave portion 50. The latter is located in the middle of the reflex zone massage stimulator shown. On each of the two convex portions 30, 40 a foot or a hand can be placed.

At the ends of the presented embodiment of the invention two projection-less portions 60 are formed having a diameter which is larger than the largest diameter of the active surface 20. During use the reflex zone massage stimulator is preferably placed on a surface such as a floor to allow it to roll over both projection-less portions 60, without the projections 21, 22 touching the floor's surface. To increase the stability, the projection-less portions 60 are provided with elastic rings 70 made of, for instance, plastic or rubber, said rings being preferably admitted in grooves 80 which are provided in the surface of the projection-less portions 60.

By placing the reflex zone massage stimulator on a surface and by, for instance, placing one or both feet on the reflex zone massage stimulator and by moving said reflex zone massage stimulator to and fro, the reflex zone massage stimulator rolls along under the foot, and in this manner massages this foot. This foot massage may be carried out without the assistance of another person and while being otherwise occupied, such as while watching television. The provision of the two supporting projection-less portions 60 at the ends of the reflex zone massage stimulator makes said reflex zone massage stimulator especially stable, which stability is even enhanced by providing elastic rings 70, which are placed around the projection-less portions 60. When the massage stimulator now rolls over the floor it has a better grip on the floor and sliding is prevented. The production of noise when rolling on hard surfaces is also reduced thanks to the application of the elastic rings 70. To prevent the rings 70 from sliding off the projection-less portions 60, said rings are admitted into grooves 80 which are provided in the projection-less portions 60 having a larger diameter.

It can be seen that in relation to each other, the two convex portions 30, 40 have a different degree of convexity. The objective of this is to provide the possibility of stimulating, for instance, the foot in different ways during massage. Obviously both portions may also possess an equal degree of convexity. Because the various portions of the active surface undergo a gradual transition, the active surface next to the convex portions curves upward again. These gradual transitions 31, 41 are now shaped such that when one foot is placed on a convex portion 30, 40 for the foot sole to be massaged, the round side part at the underside of the foot is also stimulated.

Due to the convex portion 50 in the middle of the preferred embodiment of the reflex zone massage stimulator, other parts of, for instance, the foot such as, for instance, the heel or the toes of the foot may receive extra stimulation. A consequence of the transition of the substantially concave portion to the convex portions is that thickenings 51 are formed. On either side of said thickenings 51 a toe may be placed to be massaged.

At the outside of the rod-like element the reflex zone massage stimulator is in the longitudinal direction provided with a plurality of electrode strips 15 having electrode projections 22. The rows of electrode projections 22 thus formed in the longitudinal direction of the rod-like element are provided alternating (not shown) with rows of non-electrode projections 21. The electrode strips are electrically connected with an electro-neuro stimulator pulses-generating device 90 fed by an, optionally rechargeable, storage battery or battery 91. Preferably the device is used on low voltage and weak current in order to ensure, among other things, operational safety.

The device 90 generates electro-neuro stimulator pulses which are fed to the electrode projections 22 in order to provide extra stimulation for the reflex zones via the skin, for a better and quicker effect of the reflex zone massage stimulator. Owing to this the reflex zone massage stimulator has become a Transcutane Electro-NeuroStimulator (TENS).

It is also possible to position the device 90 separate from the massage stimulator and to connect said device with the massage stimulator by means of a cable in order to feed the electro-neuro stimulator pulses to the electrode projections.

The massage is the most effective if the projections 21, 22 possess a certain elasticity. The projections 21, 22 are preferably made from a plastic having a Shore hardness of about 75. The length of the projections 21, 22 which are formed as rodlets and which project from the surface of the rod-like body, is preferably about 4 mm and the diameter of the rodlets is about 3.2 mm.

In the preferred embodiment the rod-like element 10 and the non-electrode projections 21 are manufactured as one part and from one material. This streamlines the production, but also prevents that the projections 21 loosen and come out. Of course, it is also possible to manufacture the rod-like element from a metal such as, for instance, aluminium, or from wood and to provide recesses in which the projections may be fixed.

It is also possible, in case the rod-like element is manufactured from an elastic material, to have the elastic rings 70 which are provided around the projection-less portions 60 form one part with the rod-like element 10 manufactured from one material. This results in a further streamlining of the production. Of course, it is also possible to manufacture the rod-like element 10, the elastic rings 70 and the non-electrode projections 21 as one part from one material. Now one mould suffices to make this part.

The embodiment discussed here must not be understood to limit the invention to this embodiment. It is, for instance, possible to place the projections not straight but inclined on the surface of the rod-like body. Another possibility is to use suction cups as projections 21, 22 or a combination of suction cups and rodlets.

What is claimed is:

1. A reflex zone massage stimulator, particularly for the hand or the foot, comprising a rotatable rod-like element comprising projections, an envelope formed by the ends of said projections defining an active surface to be brought into contact with skin of a user, and said active surface being curved such that, viewed in a longitudinal direction of said rod-like element, a distance from said active surface to a rotation axis of said rod-like element varies, and comprising a plurality of portions for stimulating a different body part, wherein said projections are rodlets and are made from a plastic having a Shore hardness of about 50 to 90 and said active surface comprises two substantially convex portions for stimulating a first body part, both ends of said convex portions being adjacent to rounded portions which are oriented for stimulating a side of said first body part, and said convex portions being intervened by a substantially concave portion for stimulating a second, smaller body part.

2. A massage stimulator according to claim 1 wherein a plurality of said rodlets are formed as electrode rodlets connected to a pulse-generating device to convey electro-neuro stimulator pulses via the skin to reflex zones of the user.

3. A massage stimulator according to claim 2 wherein a plurality of rows of said electrode rodlets are provided in the longitudinal direction of and around said rod-like element, alternating with rows of non-electrode rodlets provided in said longitudinal direction of said rod-like element.

4. A massage stimulator according to claim 3 wherein said rod-like element and non-electrode rodlets are manufactured as one part from one material.

5. A massage stimulator according to claim 2 wherein said said pulse-generating device and a battery as a power-supply for said pulse-generating device are housed within said rod-like element.

6. A massage stimulator according to claim 2 wherein said electrode rodlets are connected with an electrode strip.

7. A massage stimulator according to claim 6 wherein said electrode rodlets and said electrode strip are for unitary.

8. A massage stimulator according to claim 1 wherein a longitudinal portion of said rod-like element has a constant diameter while length of the projections varies.

9. A massage stimulator according to claim 1 wherein said active surface comprises at least two substantially convex portions which in relation to each other possess a different degree of convexity.

10. A massage stimulator according to claim 1 wherein said active surface comprises at least two substantially concave portions which in relation to each other possess a different degree of convexity.

11. A massage stimulator according to claim 1 wherein the massage stimulator comprises one or more projection-less portions having a diameter which is larger than a largest diameter of said active surface.

12. A massage stimulator according to claim 11 comprising two projection-less portions having a larger diameter than a largest diameter of the active surface and positioned at ends of the element.

13. A massage stimulator according to claim 11 wherein said projection-less portions are provided with a surrounding elastic element.

14. A massage stimulator according to claim 13 wherein said elastic element is a ring partially admitted into a groove provided in a surface of said projection-less portions.

15. A massage stimulator according to claim 1 wherein a transition between said convex portions is gradual.

16. A massage stimulator according to claim 1 wherein said projections are placed substantially perpendicular to a surface of said rod-like element.

17. A massage stimulator according to claim 1 wherein said projections are made from an elastic material.

18. A massage stimulator according to claim 1 wherein said projections are made from a plastic having a Shore hardness of about 75.

19. A massage stimulator according to claim 1 wherein said rodlets project about 4 mm from a surface of said rod-like element.

20. A massage stimulator according to claim 1 wherein a diameter of said rodlets is about 3.2 mm.

21. A reflex zone massage stimulator, particularly for the hand or the foot, comprising a rotatable rod-like element comprising projections, an envelope formed by the ends of said projections defining an active surface to be brought into contact with skin of a user, and said active surface being curved such that, viewed in a longitudinal direction of said rod-like element, a distance from said active surface to a rotation axis of said rod-like element varies, and comprising a plurality of portions for stimulating a different body part, wherein said projections are rodlets and said active surface comprises two substantially convex portions for stimulating a first body part, both ends of said convex portions being adjacent to rounded portions which are oriented for stimulating a side of said first body part, and said convex portions being intervened by a substantially concave portion for stimulating a second, smaller body part, wherein a plurality of said rodlets are formed as electrode rodlets connected to a pulse-generating device to convey electro-neuro stimulator pulses via the skin to reflex zones of the user, and wherein a plurality of rows of said electrode rodlets are provided in the longitudinal direction of and around said rod-like element, alternating with rows of non-electrode rodlets provided in said longitudinal direction of said rod-like element.

22. A massage stimulator according to claim 21 wherein said rod-like element and non-electrode rodlets are manufactured as one part from one material.

23. A reflex zone massage stimulator, particularly for the hand or the foot, comprising a rotatable rod-like element comprising projections, an envelope formed by the ends of said projections defining an active surface to be brought into contact with skin of a user, and said active surface being curved such that, viewed in a longitudinal direction of said rod-like element, a distance from said active surface to a rotation axis of said rod-like element varies, and comprising a plurality of portions for stimulating a different body part, wherein said projections are rodlets and said active surface comprises two substantially convex portions for stimulating a first body part, both ends of said convex portions being adjacent to rounded portions which are oriented for stimulating a side of said first body part, and said convex portions being intervened by a substantially concave portion for stimulating a second, smaller body part, wherein the massage stimulator comprises one or more projection-less portions having a diameter which is larger than a largest diameter of said active surface, and wherein said projection-less portions are provided with a surrounding elastic element.

24. A massage stimulator according to claim 23 wherein said elastic element is a ring partially admitted into a groove provided in a surface of said projection-less portions.

25. A reflex zone massage stimulator, particularly for the hand or the foot, comprising a rotatable rod-like element comprising projections, an envelope formed by the ends of said projections defining an active surface to be brought into contact with skin of a user, and said active surface being curved such that, viewed in a longitudinal direction of said rod-like element, a distance from said active surface to a rotation axis of said rod-like element varies, and comprising a plurality of portions for stimulating a different body part, wherein said projections are rodlets and said active surface comprises two substantially convex portions for stimulating a first body part, both ends of said convex portions being adjacent to rounded portions which are oriented for stimulating a side of said first body part, and said convex portions being intervened by a substantially concave portion for stimulating a second, smaller body part, and wherein said rodlets project about 4 mm from a surface of said rod-like element.

26. A reflex zone massage stimulator, particularly for the hand or the foot, comprising a rotatable rod-like element comprising projections, an envelope formed by the ends of said projections defining an active surface to be brought into contact with skin of a user, and said active surface being curved such that, viewed in a longitudinal direction of said rod-like element, a distance from said active surface to a rotation axis of said rod-like element varies, and comprising a plurality of portions for stimulating a different body part, wherein said projections are rodlets and said active surface comprises two substantially convex portions for stimulating a first body part, both ends of said convex portions being adjacent to rounded portions which are oriented for stimulating a side of said first body part, and said convex portions being intervened by a substantially concave portion for stimulating a second, smaller body part, and wherein a diameter of said rodlets is about 3.2 mm.

* * * * *